United States Patent [19]

Baumann et al.

[11] Patent Number: 5,731,896
[45] Date of Patent: Mar. 24, 1998

[54] MICROSCOPE

[75] Inventors: Hans Baumann, Raisdorf; Wolfgang Graczyk, Kiel; Uwe Hoff, Preetz; Jorg-Roger Peters, Schmalstede, all of Germany

[73] Assignee: Carl-Zeiss-Stiftung, Heidenheim, Germany

[21] Appl. No.: 170,527

[22] Filed: Dec. 20, 1993

[30] Foreign Application Priority Data

Dec. 24, 1992 [DE] Germany .............. 42 44 072.6

[51] Int. Cl.⁶ .............................. G02B 27/64; G02B 21/00
[52] U.S. Cl. ..................... 359/557; 359/368; 359/554
[58] Field of Search ..................... 359/368, 383, 359/384, 391–398, 554–557; 250/307, 308, 310, 311; 248/550, 638, 562; 318/128, 611, 623, 649, 671, 687

[56] References Cited

U.S. PATENT DOCUMENTS

| 3,577,205 | 5/1971 | Hobrough | 359/557 |
| 3,756,686 | 9/1973 | Humphrey | 359/555 |
| 5,049,745 | 9/1991 | Vogen et al. | 250/310 |

FOREIGN PATENT DOCUMENTS

| 504930 | 9/1992 | European Pat. Off. | |
| 48207 | 7/1982 | Germany | 359/368 |

*Primary Examiner*—Thong Nguyen

[57] ABSTRACT

A microscope has the optically imaging portion of its optical arrangement separated from the object to be observed. The microscope has at least one force exerting drive element for the compensation of vibrations acting on the optical arrangement from its surroundings in at least one direction perpendicular to the optical axis. The drive element is installed in or on the microscope.

26 Claims, 5 Drawing Sheets

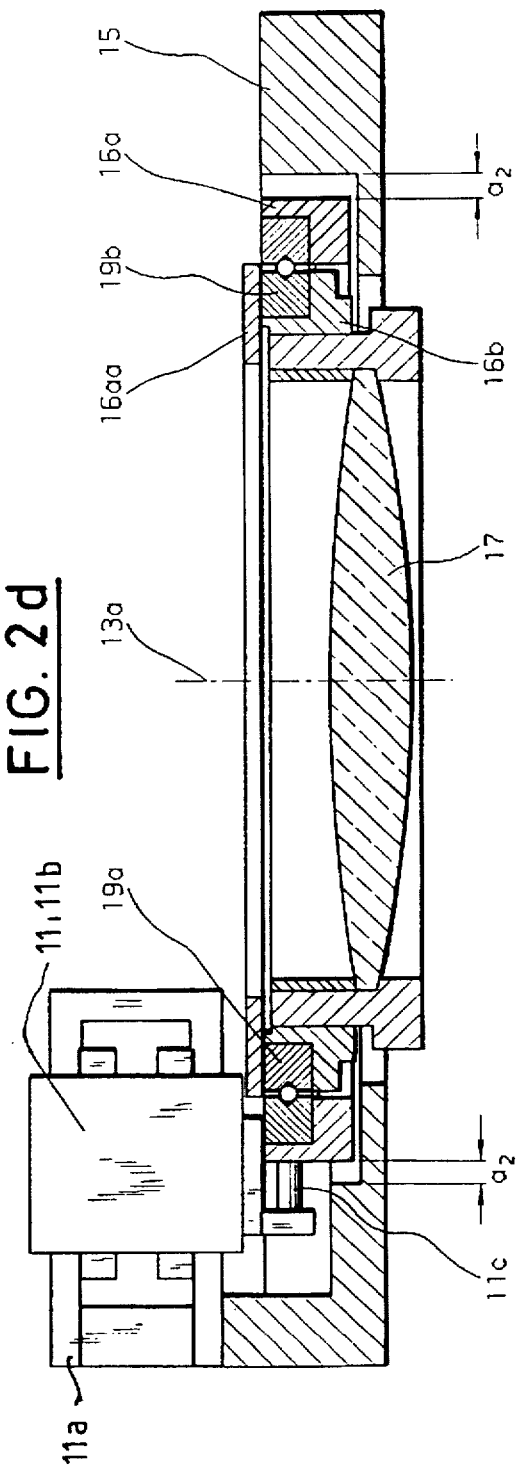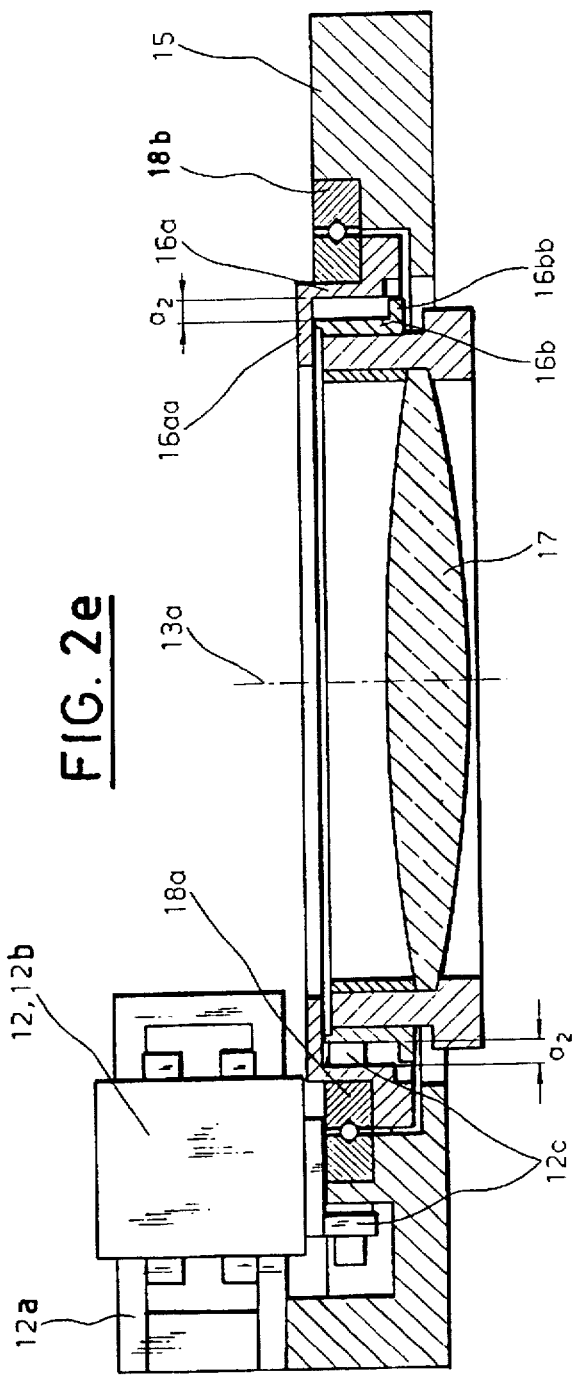

5,731,896

MICROSCOPE

BACKGROUND OF THE INVENTION

1. Field of the Invention

This invention relates to a microscope.

Optical equipment is exposed to vibrations from the surroundings. These vibrations (unintentional contact, vibrations of the building, etc.) make work difficult with this equipment, particularly when the object to be observed is not fixedly connected to the equipment.

This is particularly the case with telescopes, cameras and operation microscopes, even when these devices are mounted on stands. Operation microscopes have, in general, a magnification ≦30×. Operation microscopes are frequently fastened by a boom to the floor or the ceiling. Since the boom has only a limited stiffness, operation microscopes, in particular, tend to oscillate when excited, so that work with this equipment is considerably hampered.

2. Relevant Prior Art

Image stabilization devices are known per se. Thus, in particular, a device of this kind is known from European Patent 504,930, in which an x-y table is moved by a motor via spindles. The indirect drive via spindles has the disadvantage that the adjustment is neither immediate nor precise. This greatly reduces the utility value of the device. In addition, the thread wears in use, so that deterioration of the accuracy of adjustment is to be expected after a time.

SUMMARY OF THE INVENTION

The object of the invention is to provide a microscope in which image movement brought about by vibration of the microscope, in particular, transverse motions perpendicular to the optical axis, are suppressed as far as possible.

This object is achieved by a microscope having an optical arrangement in which at least an optically imaging portion of the optical arrangement is separated from the object to be observed. The microscope includes a sensor for sensing vibrations, an electronic circuit for converting signals from the sensor to signals for a drive element, and at least one drive element installed in or on the microscope and connected to the electronic circuit for compensating vibrations acting on the optical arrangement from its surroundings.

Decoupling of the microscope from the vibrations from its surroundings is brought about for the first time by the inventive design of the microscope.

Normally, these vibrations are rather long waved, so that a vibration compensation that uses only the acceleration of masses provides unsatisfactory results. However, other active systems for vibration compensation do not take into account, or insufficiently take into account, the long wave vibrations acting on fastened or standing equipment from the surroundings.

Here compensation takes place in at least one direction perpendicular to the optical axis.

Advantageously, coupling between the drive element and the driven part is fixed, in order to avoid transmission losses and ensure a rapid, precise reaction to vibrations of the microscope caused by the surroundings.

Preferably the objective is decoupled with respect to the microscope housing and the ocular.

To compensate for all transmissions of vibration from the surroundings of the microscope, it is advantageous to have the compensation take place in two degrees of freedom that are mutually perpendicular and are perpendicular to the optical axis. In this manner, movement in the image plane brought about by vibrations can be influenced and, with suitable means, can be compensated. Decoupling of the movement takes place such that the objective is freely movable in the housing within a plane extending perpendicular to the optical axis.

BRIEF DESCRIPTION OF THE DRAWINGS

The invention is described herein below in detail by means of a preferred embodiment, with reference to the accompanying drawings. Further important features and other possibilities of embodiment will become apparent from the description of the inventive concept.

In the drawings:

FIG. 1c shows the linear motor of FIG. 1a in a front view, partially sectional along section line Ic—Ic shown in FIG. 1a;

FIG. 2b shows an objective mounting in the y-direction in plan view from FIG. 2a;

FIG. 2c shows an objective mounting in the x-direction in plan view from FIG. 2a;

FIG. 2d shows a sectional view through the objective mounting of FIG. 2a in the y-direction along section line IId—IId shown in FIG. 2b;

FIG. 2e shows a sectional view through the objective mounting of FIG. 2a in the x-direction along section line IIe—IIe shown in FIG. 2c;

DETAILED DESCRIPTION OF A PREFERRED EMBODIMENT

Figure 1A:
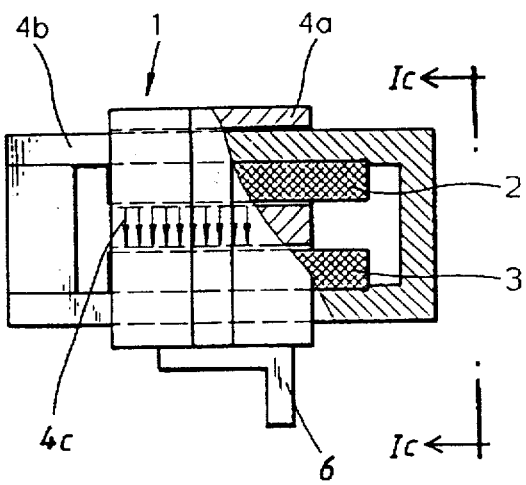
FIG. 1a shows a linear motor in partial section.
Figure 1B:
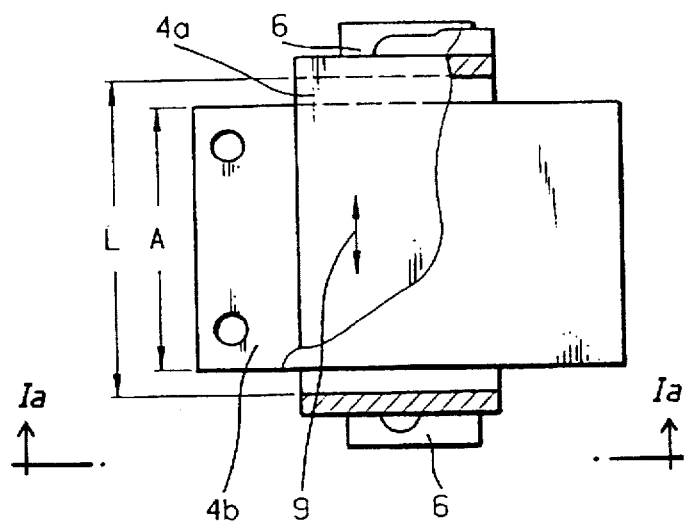
FIG. 1b shows the linear motor of FIG. 1a in plan view, partially sectional along section line Ia—Ia shown in FIG. 1b.
Figure 1C:
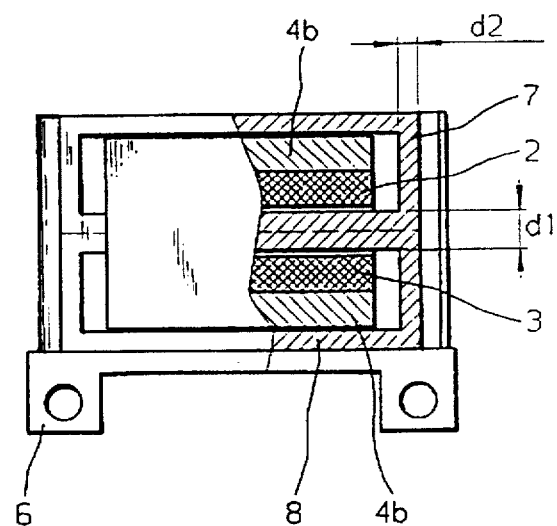
Figure 1D:
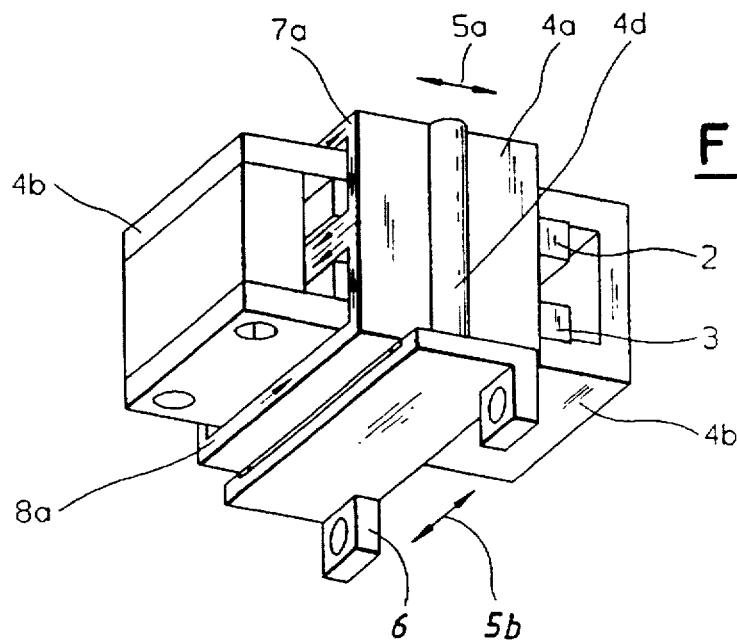
FIG. 1d shows the linear motor of FIG. 1a in perspective view.
Figure 2A:
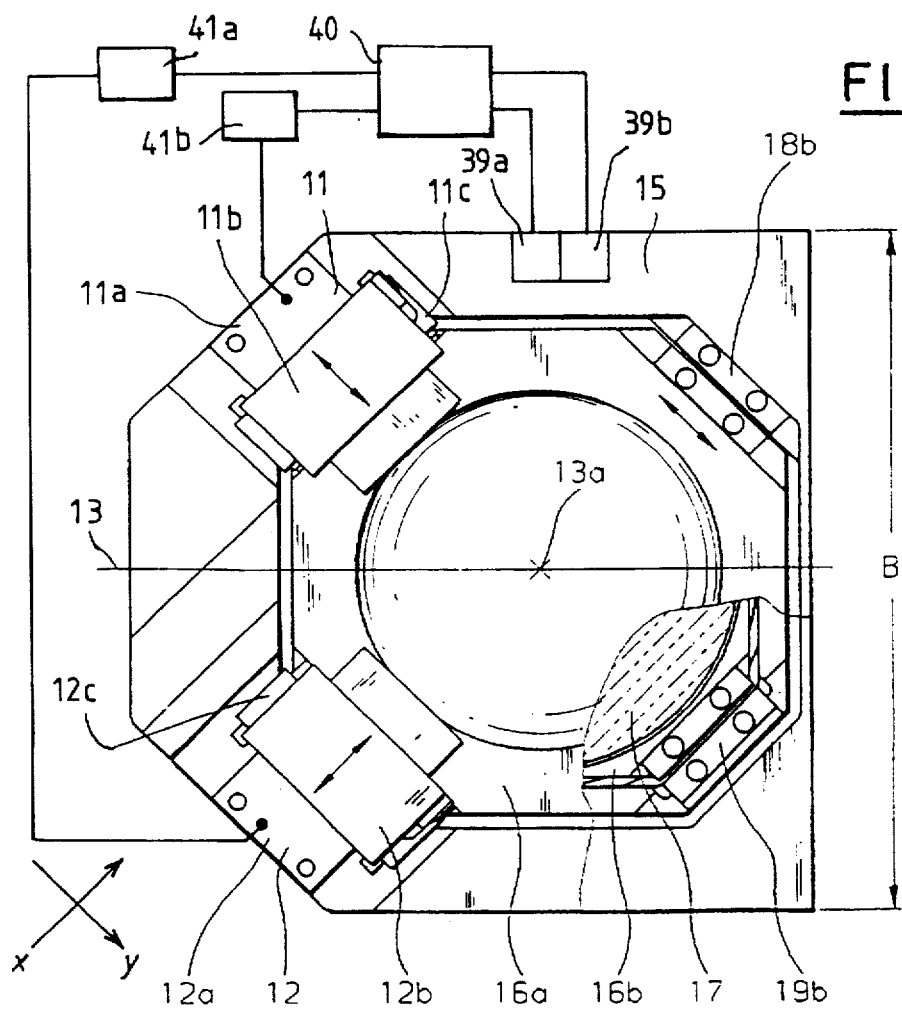
FIG. 2a shows a stabilizing objective mounting in plan view, partially sectional.
Figure 2B:
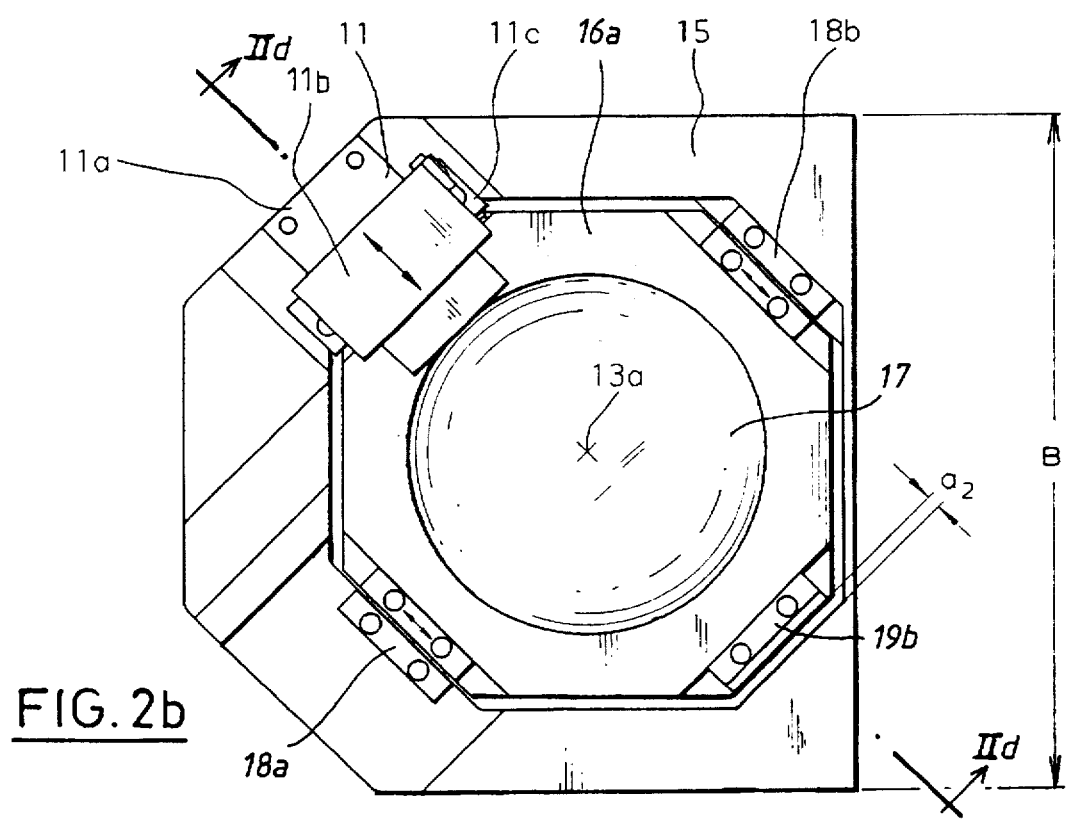
Figure 2C:
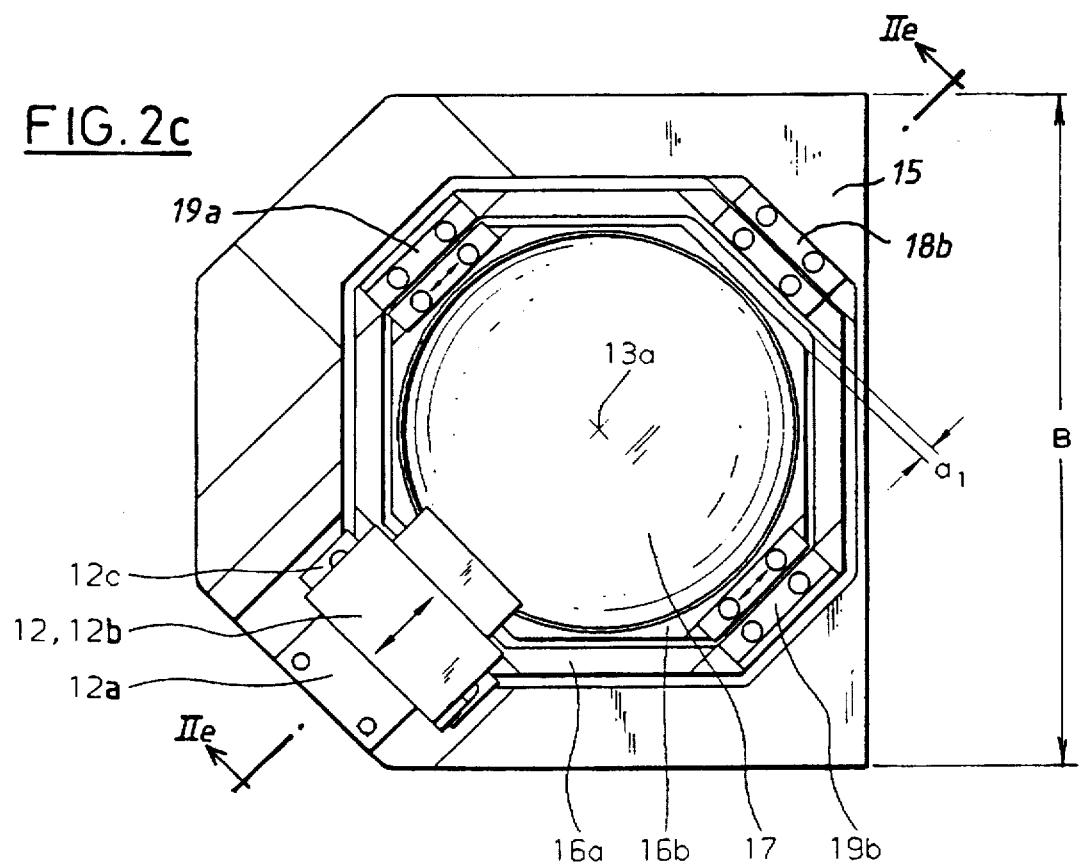

A linear motor (1) used as a drive element is shown in FIGS. 1a–d. This linear motor (1) has as essential components a coil device (4a), a stator (4b) and two permanent magnets (2, 3).

The stator (4b) is preferably a closed, U-shaped base body of a high-permeability material, such as Vacoflux. The rectangular permanent magnets (2, 3) are installed on the inner side of the two rectangularly shaped arms of the stator (4b) such that the north pole of the permanent magnet (2) is opposite the south pole of the permanent magnet (3). A nearly homogeneous magnetic field with field lines (4c) that run perpendicularly is thereby formed between the two permanent magnets (2, 3).

The coil device (4a), also termed "rotor," is formed by a double rectangular coil, the turns of which (not drawn in the Figure) run perpendicularly to the active direction of motion (5a) of the coil device (4a) and perpendicular to the field lines (4c) of the permanent magnets (2, 3). The form of the coil device (4a) is such that one half (7a) of the coil passes over the stator (4b) and the other half (8a) of the coil passes under the stator (4b). The coil halves (7a and 8a) are cast together unsupported including the fastening device (6) (which is used to move the objective mounting, as described below). The internal width (L) of the coil device (4a) is greater than the external width (A) of the stator (4b). The coil device (4a) thereby has two degrees of freedom. On the one hand, there is a degree of freedom in the direction of motion (5a) that results from the action of the force of the magnetic field of the permanent magnets (2, 3) on the coil device (4a) through which current is flowing. On the other hand, there is a degree of freedom in a direction of motion (5b) perpendicular to the first direction of motion (5a), due to the larger internal width (L) of the coil body, without affecting the mode of action of the linear motor (1).

The coil device (4a) is without a core, in order to simultaneously minimize weight and volume and obtain a maximum packing density of the coil device (4a) with minimized air gaps between the rotor and the stator, especially in the field of force of the field lines (4c). This achieves the maximum possible drive forces of the linear motor (1). The coil device (4a) is a double rectangular coil from two individual rectangular coils (7, 8), the turns (7a, 8a) being divided half between each individual coil.

To produce the coil device (4a), each of the two rectangular coils (7, 8) is wound on a suitable mandrel with the required cross section. Thereafter, the coils (7, 8), including the fastening device (6), are assembled into a mold and cast together. The coil device (4a) thus obtained has an optimum mechanical strength and thermal conductivity, with maximum packing density and minimized construction volume.

The effective surface for carrying heat away is increased by about 60% in this double coil body (4a) in comparison with a single rectangular coil, in which the turns are not divided.

A further increase in the liberation of heat is achieved by profiling (4d) on the coil body (4a), produced in a casting mold.

The coil body (4a) has different coil thicknesses, (d1, d2), wherein d2=d1/2.

By the division of the turns (7a, 8a) that encircle the stator (4b), the coil width is reduced by d1=2×d2.

A further increase in the relationship of power to volume is achieved by the use of coil wire with a square cross section.

The turns (7a, 8a) in the coil device do not run exactly perpendicular to the limiting direction (5a) because of the required forward feed during winding. The transverse component that thereby arises can be largely compensated in the double coil body, in that the two coil halves are wound with a different sense of winding and subsequently cast. The transverse component of the one half then largely cancels the transverse component due to the inclined lay of the turns in the other half in the opposite direction.

The installation of two linear motors (11, 12) shown in FIGS. 1a–1d and the objective mounting is described in FIGS. 2a–2e.

To minimize space requirements, the motors (11, 12) are arranged offset at a 45° angle to the mid plane (13) of an adapter. The adapter width (B) can thereby be kept to a minimum. The stator (11a, 12a) is fixedly connected to a base-plate (15) of the adapter. The double coil (11b) is connected via a fastening device (11c) to an intermediate ring (16a), which is designed as a table guide in the y-direction. As against this, the double coil (12b) is connected by means of the fastening device (12c) through the intermediate ring (16a) to an objective holder (16b) designed as a table guide in the x-direction.

An objective (17) is received by the octagonal objective holder (16b), which is in an inner location and permits a motion of the objective (17) in the x-direction. The optical axis (13a) of the objective (17) is located exactly in the center of the objective holder (16b) into which the objective (17) is screwed. The objective holder (16b) is connected to the intermediate ring (16a), for as little friction as possible, by means of two linear guide pairs (19a, 19b). Motion of the inner objective holder (16b) relative to the intermediate ring is only possible in one direction, i.e., the x-direction.

The objective holder (16b) has a free space (all in the x-direction available for motion of the objective within the intermediate ring (16a). In the y-direction, which is perpendicular to the x-direction, the intermediate ring (16b), together with the linear guide pairs (18a, 18b) installed on it, has a free space (a₂), which is available for motion of the objective (17) in the y-direction.

The mutually opposed linear guide pairs (18a, 18b) of the intermediate ring (16a) are arranged offset by 90° with respect to the two linear guide pairs (19a, 19b) of the objective holder (16b), and are fixedly connected to the housing (15) of the adapter. The linear guide pairs (18a, 18b and 19a, 19b, respectively) are designed such that the objective (17) can move easily in both the x-direction and y-direction.

An x/y table guide system is described herein above, and permits a motion of the objective (17) diagonally to the outer limits of the housing (15) in these two directions. This x/y table guide system has a high stiffness with minimum construction masses, with the center remaining free in order not to intersect the optical beam path through the objective (17) in the z-direction.

The resulting interleaved type of construction is shown in FIGS. 2d and 2e. Here in particular the inward-drawn collar (16aa) of the outer intermediate ring (16a) contributes to increasing the stiffness, without thereby increasing the construction size. This collar (16aa) can be modified in its geometry and optimized according to the conditions for its incorporation. The same holds for the construction form of the inner objective ring (16b) and for the reinforcing collar (16bb) located on it.

The components of the mechanical vibrations are measured by two acceleration sensors (39a, 39b) arranged perpendicularly to each other. The related path components are computed from the acceleration values by a double integration. The values thus obtained represent the reference values for a PID (Proportional, Integral, Differential) controller in an electronic circuit. The controller (40) controls two final power stages (41a, 41b) that are associated with the components and which drive the two linear motors (11, 12).

The linear motors (11, 12) move the objective (17) mounted in an x/y table in opposite phase to the vibrator motion. The actual value at any instant is sensed by linear path sensors associated with the components and is fed via an electronic circuit to the controller as the correction variable.

The opposite-phase deflection of the main objective (17) or of optically imaging portions greatly reduces the deterioration of the image due to the vibration of the whole microscope. This deterioration is otherwise subjectively perceived even in the magnification range ≤30× with an ideally adjusted microscope. The observer's eye in the exit pupil of the microscope can no longer follow the image motions enlarged by the magnification factor, so that the image quality is subjectively perceived as very bad. In contrast to this, a relative motion of the main objective (17) indeed leads objectively to a slightly worse image quality, but subjectively to an essentially better image, considered as a whole. The image motion is so greatly reduced that the eye can again follow the structural details, and an image is only then perceived. With a stationary microscope, i.e. not subjected to vibrations, the objective is adjusted in the optical axis (13a), and the same image quality is achieved as with a normal microscope.

The embodiment described in FIGS. 2a–2e ensures that solely in the case of vibrating microscopes, i.e., at a measured acceleration value within a plane perpendicular to the optical axis of the objective, does a response (i.e., a contrary motion) take place.

This means that in the case of approximately constant translational motions with negligible acceleration values, no motion compensation takes place, since the eye can follow the change of the image. On the other hand, in the case of inadvertent vibrations with corresponding acceleration values, for example in the higher magnification range, an image is in fact subjectively perceived, due to the motion compensation which is brought into action.

Figure 3A:
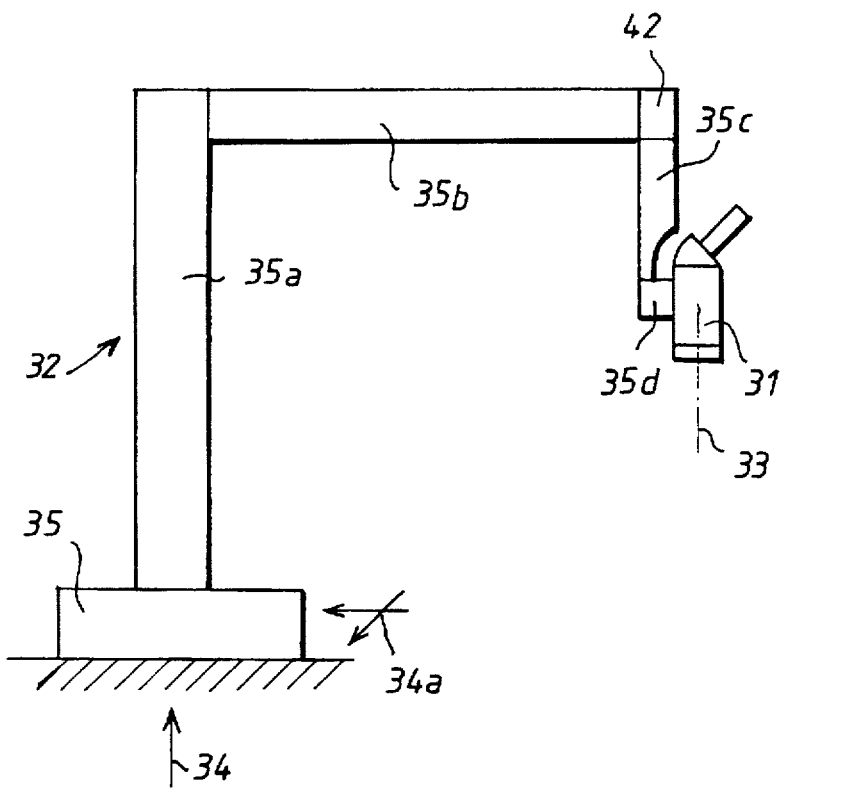
FIG. 3a shows an operation microscope on a stand.
Figure 3B:
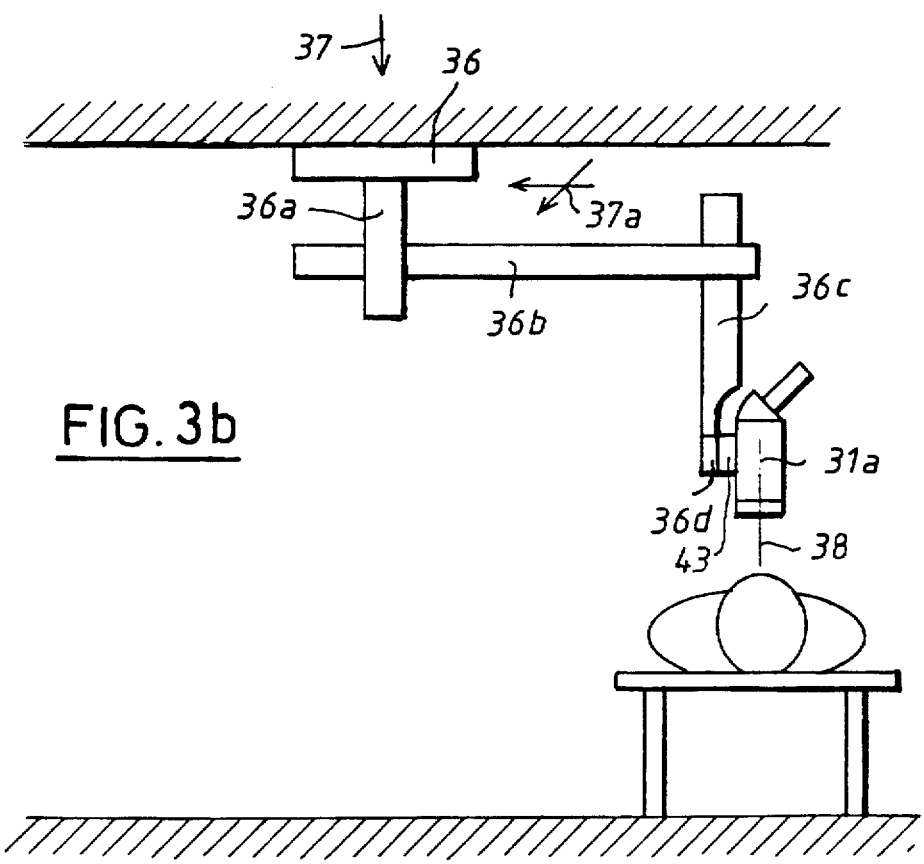
FIG. 3b shows an operation microscope on a ceiling suspension.

An operation microscope (31, 31a) in conventional suspensions, as are usual in an operating theater, is shown in FIGS. 3a and 3b.

If the operation microscope (31) is fastened to a stand (32), both axial (34) and transverse (34a) forces act on the stand foot (35). These forces (34, 34a) then lead to a corresponding motion of the operation microscope (31), because the forces (34, 34a) are transmitted by components (35a, 35b, 35c, 35d) of the stand (32).

Even when the operation microscope (31a) is fastened to the ceiling of an operating theater with a ceiling suspension, the axial and transverse forces (37, 37a) are transmitted to the operation microscope (31a) by a ceiling anchoring (36) and components (36a, 36b, 36c, 36d) of the ceiling suspension (36).

A decoupling of the operation microscope (31, 31a) can now take place:

a) with a force exerting device (42) between the vertical load-bearing column (35c, 36c) and the horizontal load-bearing bracket (35b, 36b);

b) with a force exerting device (43) between the vertical load-bearing column (35c, 36c) and the operation microscope (31, 31a);

c) with a force exerting device in the operation microscope (31, 31a).

Accordingly, the objective in the microscope ocular is decoupled from the microscope housing and microscope ocular.

Force exerting devices (42, 43) are the same as the x-y tables shown in FIGS. 2a–2e using drive motors (11, 12). Force exerting devices are used without an optical lens.

In the examples in FIGS. 2a–2e, decoupling in the operation microscope (31, 31a) is carried out with respect to transverse vibrations, because the definition of the image of the operation microscope (31, 31a) normally makes it unnecessary to eliminate the axial vibrations in the optical axis of the operation microscope (31, 31a). If these axial vibrations are also to be eliminated, this can be accomplished by known automatic focusing devices.

The particular advantage of eliminating the transverse vibrations in the operation microscope (31, 31a) is that the masses to be moved are very small. The compensating device therefore can be very compact and can be designed as an adapter. This advantage is supplemented by a rapid reaction time of the system.

We claim:

1. A microscope having an optical arrangement defining an optical path, in which said microscope is a light-optical microscope, and at least an optically imaging portion of said optical arrangement is separated from an object to be observed, comprising:

a sensor for sensing vibrations, an electronic circuit for converting signals from said sensor to signals for a drive element, and at least one drive element attached to said microscope, arranged outside said optical path and connected to said electronic circuit for compensating vibrations acting on said optical arrangement from its surroundings, said drive element being arranged to act directly on a single optical element of said optical arrangement.

2. Microscope according to claim 1, wherein said drive element has a drive direction aligned perpendicular to said optical path.

3. Microscope according to claim 1, further comprising a driven portion fixedly coupled to said drive element.

4. Microscope according to claim 1, further comprising a housing, wherein said optical arrangement includes an objective, and an ocular and said drive element decouples said objective from said housing and said ocular.

5. Microscope according to claim 1, wherein said optical arrangement includes an objective, wherein said objective is decoupled from said at least one drive element in two degrees of freedom perpendicular to said optical path.

6. Microscope according to claim 1, wherein said drive element comprises a linear motor.

7. Microscope, according to claim 6, wherein said linear motor comprises a coil device having a substantial plurality of turns, a stator and two permanent magnets.

8. Microscope according to claim 7, wherein said stator comprises a U-shaped base body.

9. Microscope according to claim 8, wherein said stator comprises a closed U-shaped base body.

10. Microscope according to claim 7, wherein said stator has two arms and said two permanent magnets are respectively attached to said two arms of said stator, the north pole of one permanent magnet being located opposite the south pole of the other permanent magnet.

11. Microscope according to claim 7, wherein said coil device comprises a double rectangular coil.

12. Microscope according to claim 7, wherein said stator has an external width (A) and said coil device has an internal width (L) that is greater than said external width (A) of said stator.

13. Microscope according to claim 7, wherein said coil device is coreless.

14. Microscope according to claim 7, wherein said coil device has a profiling.

15. Microscope according to claim 7, wherein said turns of said coil device are comprised of coil wire having a rectangular cross section.

16. Microscope according to claim 1, comprising at least two drive elements arranged at an angle of approximately 90° relative to each other in a plane perpendicular to said optical path.

17. Microscope according to claim 1, wherein said drive element is located within said microscope.

18. Microscope according to claim 17, further comprising a housing and an objective mounting movable relative to said housing in at least one direction perpendicular to said optical path, wherein said drive element includes a first portion fixedly connected to said housing and a second portion fixedly connected to said objective mounting.

19. Microscope according to claim 18, wherein said objective mounting comprises two movable mountings oriented along an x-axis and a y-axis respectively, said x-axis and said y-axis being oriented perpendicular to each other and to said optical axis, said two movable mountings being arranged such that they do not interfere with each other in their motions.

20. Microscope according to claim 19, wherein each of said two movable mountings has a sufficiently free optical opening around said optical axis to enable an optical beam to pass through said movable mounting.

21. Microscope according to claim 19, wherein each of said two movable mountings has two mutually opposite linear guides, the two linear guides of one mounting being arranged offset by 90° relative to the two linear guides of the other mounting.

22. Microscope according to claim 1, wherein said microscope comprises an operation microscope.

23. Microscope according to claim 1, wherein said at least one drive element is arranged to compensate at least vibrations perpendicular to said optical path.

24. Microscope according to claim 23, wherein said at least one drive element is arranged to compensate vibrations along said optical path.

25. Microscope according to claim 1, further comprising an objective mounting and at least one main objective lens fastened in said objective mounting, said drive element affecting a displacement of said objective mounting.

26. Image stabilizing device according to claim 1, wherein said sensor for sensing vibration comprises an acceleration sensor.

* * * * *